(12) United States Patent
Leneau

(10) Patent No.: US 8,080,535 B2
(45) Date of Patent: *Dec. 20, 2011

(54) HYALURONIC ACID NUTRITIONAL SUPPLEMENTS AND METHODS OF USING THE SAME

(75) Inventor: Harry Leneau, Jasper, MO (US)

(73) Assignee: Leneau Holdings, LLC, Jasper, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/645,237

(22) Filed: Dec. 22, 2009

(65) Prior Publication Data

US 2010/0168059 A1    Jul. 1, 2010

Related U.S. Application Data

(63) Continuation of application No. 10/629,880, filed on Jul. 29, 2003, now Pat. No. 7,635,489, which is a continuation-in-part of application No. 09/860,425, filed on May 18, 2001, now Pat. No. 6,607,745.

(51) Int. Cl.
*A61K 31/715* (2006.01)
*A61K 31/728* (2006.01)

(52) U.S. Cl. .......................... 514/54; 424/452

(58) Field of Classification Search .................. 424/452; 514/54

See application file for complete search history.

(56) References Cited

U.S. PATENT DOCUMENTS

| | | | |
|---|---|---|---|
| 4,303,676 A | 12/1981 | Balazs | |
| 4,808,576 A | 2/1989 | Schultz et al. | |
| 5,470,578 A | 11/1995 | Aoki et al. | |
| 5,633,003 A | 5/1997 | Cantor | |
| 6,159,955 A | 12/2000 | Asculai et al. | |
| 6,607,745 B2 * | 8/2003 | Leneau | 424/439 |
| 6,924,273 B2 | 8/2005 | Pierce | |
| 7,635,489 B2 * | 12/2009 | Leneau | 424/452 |
| 2003/0069202 A1 * | 4/2003 | Kern et al. | 514/46 |
| 2011/0020461 A1 * | 1/2011 | Leneau | 424/535 |

FOREIGN PATENT DOCUMENTS

| | | |
|---|---|---|
| JP | 9262057 | 10/1997 |
| WO | WO 92/22585 | 12/1992 |
| WO | WO 97/25051 | 7/1997 |
| WO | WO 00/44367 | 8/2000 |

OTHER PUBLICATIONS

"Hyaluronic Acid", from website www.bioiberica.com/eng/mp/hyaluronic.htm, retrieved Mar. 21, 2001.
"Hyaluronic acid", from website www/medmedia.com/02/068,htm, retrieved Mar. 21, 2001.
"Hyaluronic Acid" from website uconnsportsmed.uchc.edu/hyaluronic_acid.htm, retrieved Mar. 21, 2001.
"Hyaluronan (Hyaluronic acid, Synvise, Hyalgan)" from webstie www.midwestarthritis.com/html/hyaluronic_acid.htm, retrieved Mar. 21, 2001.
Wen, Dennis Y., "Intra-articular Hyaluronic Acid Injections for Knee Osteoarthritis", American Family Physician, 60, 565-70, 572 (2000).
Marte, Jim, "Green Plaster, A Webpage Resource for Orthopaedic Technologists, Infra-Articular Hyaluronic Acid Injections for Kenn Osteoarthritis", from website home.earthlink, retrieved Mar. 29, 2001.
"Arthritic Disorders", www/advanhealth.com/arthritis.htm, retrieved Mar. 29, 2001.
Arthritic Disorders and Treatments, from website, www.acfas.org/brarthdis.html retrieved Mar. 29, 2001.
"Hillbrook Wellness Institute", from website www.hillbrook.com, retrieved Mar. 23, 2001.
"Glucosamine and Chondroitin", from website chemistry.about.com/science/chemistry/library/weekly/aa120400a.htmi, (Dec. 2000), retrieved Mar. 21, 2001.
"Fibromyalgia Basics-Symptoms, Treatments and Research", from website www.fmnetnews.com/pages/basics.html, retrieved Jan. 29, 2002.
"Hyaluronic Acid (Hyaluronan)", from website, www.fidiapharma.it/site/html/hyaluronic.htm, retrieved Mar. 21, 2001.

* cited by examiner

*Primary Examiner* — Robert A Wax
*Assistant Examiner* — Aradhana Sasan
(74) *Attorney, Agent, or Firm* — Ice Miller LLP

(57) ABSTRACT

Hyaluronic acid nutritional supplements and methods of using the same. In at least one embodiment of a nutritional supplement of the present disclosure, the nutritional supplement comprises a quantity of a hyaluronic acid, or a salt or digest thereof, and a food acceptable carrier.

20 Claims, No Drawings

HYALURONIC ACID NUTRITIONAL SUPPLEMENTS AND METHODS OF USING THE SAME

PRIORITY

The present U.S. continuation application is related to, and claims the priority benefit of, U.S. Nonprovisional patent application Ser. No. 10/629,880, filed Jul. 29, 2003, which issued on Dec. 22, 2009 as U.S. Pat. No. 7,635,489, which is a continuation-in-part of, is related to, and claims the priority benefit of, U.S. Nonprovisional patent application Ser. No. 09/860,425, filed May 18, 2001, which issued on Aug. 19, 2003 as U.S. Pat. No. 6,607,745. The contents of each of these applications and patents are hereby incorporated by reference in their entirety into this disclosure.

BACKGROUND

Arthritic disorders, including acute and chronic rheumatoid arthritis and osteoarthritis as well as inflammatory skeletal and musculoskeletal conditions, affect millions of people. It has been estimated that 80% of all individuals over the age of 55 suffer from some form of arthritic disorder. The most common arthritic disorder is osteoarthritis. Osteoarthritis develops gradually over time in many cases. Patients experience alternating periods of mild to moderate pain, stiffness, and swelling of the joint and periods of relatively symptom-free joint activity.

Osteoarthritis is characterized by the deterioration of cartilage that covers the ends of bones at a joint, such as the knee or hip. In the healthy joint, cartilage acts as a shock absorber and aids the joint in bearing the stress of physical movement. In addition, synovial joint fluid produced by the synovial membrane lubricates the joint providing a slippery surface over which the bones may move. But as cartilage deteriorates, the bones begin to rub against each other causing joint pain. At the same time, the concentration of hyaluronic acid in the synovial joint decreases, reducing the lubrication ability of the synovial joint fluid. Also, joint movement may be restricted as bone ends erode or thicken, and the bones may develop painful outgrowths, or bone spurs, as a result of this erosion or thickening. If left untreated, cartilage deterioration can seriously weaken the joint, possibly to the point of deformity.

Current methods of reducing pain in osteoarthritic joints include treatment with analgesics or anti-inflammatory medications, physical therapy, topical application of hyaluronic acid to the joint, and intra-articular injection of hyaluronic acid directly into the joint. The primary goal of treatment is reduction of pain and maintenance of joint function and strength. Intra-articular injections of hyaluronic acid, known as viscosupplementation, have seen wide use for patients who have not responded well to other therapies.

Fibromyalgia is a common disabling disorder characterized by chronic musculoskeletal aches and pain, stiffness, general fatigue, and sleep abnormalities. The disorder affects 2-4% of the population and is most frequently found in women between 20 and 50 years old. The exact cause of fibromyalgia remains uncertain, and diagnosis is difficult due to the general nature of the symptoms. Currently, the most effective treatment for fibromyalgia includes a combination of analgesics, sleep aids, exercise programs, relaxation techniques and other measures to reduce muscle tension. These treatments are geared toward improving sleep quality and reducing pain.

Rheumatoid Arthritis is a chronic, systemic, inflammatory disease that chiefly affects the synovial membranes of multiple joints in the body. Rheumatoid arthritis is considered to be an autoimmune disease, in which the patient has remissions and exacerbations of the symptoms. Joints that are actively involved with the disease are usually tender, swollen, and likely demonstrate reduced motion. Several different classes of drugs are often use to treat patients with rheumatoid arthritis, including analgesics to control pain, corticosteroids, uric acid-lowering drugs, immunosuppressive drugs, nonsteroidal anti-inflammatory drugs, and disease-modifying anti-rheumatic drugs. Many patients with rheumatoid arthritis also note a decrease in their symptoms after application of heat.

BRIEF SUMMARY

The present disclosure relates to a method for relieving joint pain or other discomfort in a warm-blooded vertebrate. More particularly, the disclosure of the present application provides relief of symptoms of arthritic disorders or fibromyalgia by oral ingestion of a composition comprising an effective amount of hyaluronic acid, or a salt or digest thereof.

The present disclosure is directed to a method for relieving joint and musculoskeletal discomfort in warm-blooded vertebrates comprising the step of delivering to the vertebrate by oral ingestion a composition comprising an effective amount of hyaluronic acid, or a salt or digest thereof, and an acceptable ingestible carrier. The method is used with advantage in treating conditions associated with arthritis and for reducing the discomfort of fibromyalgia in a person afflicted with fibromyalgia.

Additional features of the present disclosure will become apparent to those skilled in the art upon consideration of the following detailed description of the preferred embodiments.

DETAILED DESCRIPTION

Hyaluronic acid is a mucopolysaccharide that is found in joint tissue and in the vitreous humor of the eye. Hyaluronic acid functions as a protective coating and a lubricant for soft tissue and joints, and additionally, helps maintain the structural integrity of soft tissue. In association with protein, hyaluronic acid binds water in the intercellular spaces and holds cells together in a jelly like matrix. This jellylike matrix provides lubrication and shock absorption throughout the body.

In the healthy knee joint, hyaluronic acid is present both in the cartilage covering the ends of bone and in the synovial joint fluid. Hyaluronic acid is usually found as part of proteoglycan aggregates in cartilage, where it helps cartilage withstand forces of weight bearing and joint movement. Hyaluronic acid is also a major component of synovial joint fluid. The synovial joint fluid provides lubrication for the cartilage against the lining of the joint and may provide some additional shock-absorption value.

Hyaluronic acid is commercially available and is prepared from the intracellular matrices of animal connective tissue, such as rooster combs and bovine tissue sources, mammalian umbilical cords, and bacterial organisms such as *streptococcus zoepidicus*. Its molecular weight ranges from about 50000 to about $8 \times 10^6$ Daltons depending on source and method of isolation. Treatment with hyaluronidases can be used to provide hydrolysates of reduced molecular weight range.

The present method provides relief from joint pain and musculoskeletal discomfort in a warm-blooded vertebrate suffering from an arthritic condition or fibromyalgia. An arthritic condition includes acute and chronic rheumatoid arthritis and osteoarthritis, as well as inflammatory conditions involving skeletal conditions and musculoskeletal conditions.

In accordance with the present disclosure, a method is provided for relieving joint or musculoskeletal pain or discomfort in a warm-blooded vertebrate comprising delivering to the vertebrate by oral ingestion a composition comprising an effective amount of hyaluronic acid, or a salt or digest thereof, and a nutritionally acceptable carrier. An "effective amount" as used herein refers to the amount of hyaluronic acid which, upon oral administration, provides relief of joint pain or discomfort. The effective amount of hyaluronic acid, or a salt or digest thereof, is from about 0.1 μ/kg to about 400 μ/kg of body weight per dose. The warm-blooded vertebrate may be a human, or an equine, canine, or feline species. In one embodiment the method is used to reduce joint pain in a person afflicted with osteoarthritis.

In another embodiment the method is used for reducing the discomfort of fibromyalgia. The hyaluronic acid, salt or digest is orally ingested with an acceptable carrier, typically an aqueous beverage or food product. Preferably, the hyaluronic acid, salts, or hydrolysates for use in the present disclosure are formulated into a liquid aqueous concentration, for example, a dietary supplement formulation, which is diluted in portions and mixed with food, water, or other beverages for oral ingestion. Alternatively the hyaluronic acid, salt, or hydrolysate can be packaged in individual solid or liquid doses, for instance in capsules or gel seals. The concentrate can contain about 1 to about 10 mg of hyaluronic acid, its salt, or hydrolysate per milliliter of concentrate. In one embodiment a dose is administered by combining 7 to 10 drops of the concentrate in a cold beverage which is consumed on conjunction with a meal, for example.

EXAMPLES

Example 1

Oral Ingestion of Hyaluronic Acid by Patients Suffering from Osteoarthritis

A study involving sixty-seven patients suffering from osteoarthritis was undertaken to determine the effectiveness of oral ingestion of hyaluronic acid. Each patient received 1-4 mg of hyaluronic acid by oral ingestion administration 1 to 4 times a day over periods ranging from about 4 to about 2 weeks, during which period the patients' subjective pain feeling was reported. Twenty-nine patients (43.3%) reported no pain after oral ingestion of hyaluronic acid, and additionally reported increased range of motion. Twenty-four patients reported (35.8%) some degree of pain relief and some increased range of motion. Fourteen patients reported no change in the amount of pain they felt.

Example 2

Oral Ingestion of Hyaluronic Acid by Patients Afflicted with Fibromyalgia

Another study involving thirty-five human patients suffering pain and discomfort associated with fibromyalgia was undertaken to evaluate the effectiveness of oral ingestion of hyaluronic acid. Each patient received about 1 to about 6 mg of hyaluronic acid by oral ingestion administration of concentrate diluted into beverages or food. Over a treatment period of about 1 to about 14 months, the patients' subjective pain feeling was reported. Twenty-one patients reported no pain after hyaluronic acid therapy. Six patients (17.1%) reported some (60%) degree of pain relief. Eight patients reported no change in the amount of pain they felt.

Example 3

Oral Ingestion of Hyaluronic Acid by Patients Afflicted with Rheumatoid Arthritis Another study involving seventeen human patients suffering pain and discomfort associated with rheumatoid arthritis was undertaken. Each patient received about 1 mg of an oral hyaluronic acid solution for a period of 30 days. Each patient was asked to evaluate his or her subjective pain feeling and report the score on a scale of 0 to 10, wherein 0 means no pain and/or stiffness whatsoever and 10 means worst imaginable pain and/or stiffness. Prior to the start of the study, the patients reported as follows:

| | |
|---|---|
| 1 patient reported | 7 |
| 8 patients reported | 8 |
| 4 patients reported | 9 |
| 2 patients reported | 10 | for an average of 8.47. At the completion of the 30-day study, the patients responded as follows:

| | |
|---|---|
| 1 patient reported | 0 |
| 1 patient reported | 1 |
| 3 patients reported | 2 |
| 7 patients reported | 3 |
| 2 patients reported | 7 |
| 1 patient reported | 10 | for an average of 3.47, which is considerably lower than the pain reported prior to treatment. Two of the seventeen patients did not respond to the questionnaire.

Given that oral ingestion of hyaluronic acid reduced join pain and other discomforts due to osteoarthritis, fibromyalgia, and rheumatoid arthritis, it is expected that oral ingestion of hyaluronic acid would reduce joint pain and stiffness resulting from a variety of conditions.

While various embodiments of hyaluronic acid nutritional supplements and methods of using the same have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A nutritional supplement, consisting essentially of:
   an effective amount of a hyaluronic acid, or a salt or digest thereof; and
   a food acceptable carrier.

2. A method for relieving joint pain or other discomforts associated with joint disorders in a warm-blooded vertebrate, the method comprising the step of:
   ingesting a nutritional supplement, the nutritional supplement consisting essentially of:
      an effective amount of a hyaluronic acid, or a salt or digest thereof; and
      a food acceptable carrier.

3. The nutritional supplement of claim 1, wherein the quantity of the hyaluronic acid, or a salt or digest thereof, is between about 1 mg to about 6 mg.

4. The nutritional supplement of claim 1, wherein the quantity of the hyaluronic acid, or a salt or digest thereof, is between about 0.1 μg/kg to about 400 μg/kg of body weight of a warm-blooded vertebrate.

5. The nutritional supplement of claim 1, wherein the nutritional supplement is provided in an orally ingestible dosage form.

6. The nutritional supplement of claim 5, wherein the orally ingestible form is a capsule or gel seal.

7. The nutritional supplement of claim 1, wherein the food acceptable carrier comprises an aqueous beverage.

8. The nutritional supplement of claim 1, wherein the food acceptable carrier comprises a food product.

9. The nutritional supplement of claim 1, wherein the nutritional supplement is formulated into an aqueous concentration.

10. The nutritional supplement of claim 9, wherein the aqueous concentration comprises a dietary supplement formulation.

11. The nutritional supplement of claim 9, wherein the aqueous concentration comprises about 1 mg/mL to about 10 mg/mL of the hyaluronic acid, or a salt or digest thereof.

12. The nutritional supplement of claim 11, wherein the aqueous concentration is diluted into a second food acceptable carrier.

13. The nutritional supplement of claim 12, wherein the food acceptable carrier and the second food acceptable carrier comprise the same material.

14. The nutritional supplement of claim 11, wherein when about 7 to about 10 drops of the aqueous concentration are diluted into an aqueous beverage, the aqueous beverage comprises about 1 mg to about 6 mg of hyaluronic acid, or a salt or digest thereof.

15. The method of claim 2, wherein the warm-blooded vertebrate is a human, or an equine, canine, or feline species.

16. The method of claim 2, wherein the joint pain is the result of a condition selected from the group consisting of an arthritic condition and an inflammatory condition.

17. The method of claim 2, wherein the quantity of the hyaluronic acid, or a salt or digest thereof, is between about 1 mg to about 6 mg.

18. The method of claim 2, wherein the quantity of the hyaluronic acid, or a salt or digest thereof, is between about 0.1 μg/kg to about 400 μg/kg of body weight of a warm-blooded vertebrate.

19. The method of claim 2, wherein the step of ingesting a nutritional supplement is performed by orally ingesting the nutritional supplement.

20. A concentrated nutritional supplement, comprising:
   an effective amount of a hyaluronic acid, or a salt or digest thereof; and
   a food acceptable carrier;
   wherein the concentrated nutritional supplement, when diluted into solid or liquid food, has a diluted amount of hyaluronic acid, or a salt or digest thereof, of about 1 mg to about 6 mg.

* * * * *